(12) United States Patent
Nakazawa et al.

(10) Patent No.: US 8,399,038 B2
(45) Date of Patent: Mar. 19, 2013

(54) METHOD FOR PRODUCING DRIED MICROBIAL CELLS

(75) Inventors: Hidetsugu Nakazawa, Kawasaki (JP); Togo Hotta, Kawasaki (JP); Hiroyuki Sato, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 255 days.

(21) Appl. No.: 12/147,677

(22) Filed: Jun. 27, 2008

(65) Prior Publication Data

US 2008/0292762 A1 Nov. 27, 2008

Related U.S. Application Data

(63) Continuation of application No. PCT/JP2006/326361, filed on Dec. 27, 2006.

(30) Foreign Application Priority Data

Dec. 28, 2005 (JP) ................................. 2005-378818

(51) Int. Cl.
*A47J 39/00* (2006.01)
*A23C 9/12* (2006.01)
*A23L 1/18* (2006.01)
*A23B 4/03* (2006.01)

(52) U.S. Cl. ............ 426/520; 426/61; 426/448; 426/465
(58) Field of Classification Search .................... 426/61, 426/465, 520, 448
See application file for complete search history.

(56) References Cited

U.S. PATENT DOCUMENTS

| | | | |
|---|---|---|---|
| 3,843,807 A * | 10/1974 | Ridgway, Jr. ................... | 426/61 |
| 6,432,468 B1 * | 8/2002 | Akimoto et al. ............... | 426/614 |
| 6,706,278 B1 * | 3/2004 | Tsubokura et al. ........... | 424/442 |
| 7,365,161 B2 | 4/2008 | Kumagai et al. | |
| 2009/0326267 A1 * | 12/2009 | Bijl et al. ....................... | 562/512 |

FOREIGN PATENT DOCUMENTS

GB 2123833 * 2/1984

OTHER PUBLICATIONS

NPL "Dried Microbial Cells" by Laroche C and Gervias P in "Unexpected thermal destruction of dried , glass bead-immobilized microorganisms as a function of water activity" 69(5): p. 3015-3019, 2003.*
NPL "Aw and water content", retrieved on Jun. 4, 2010.*
NPL "Dry *E coli*" : Tsuji K et al. entitled "Dry-Heat destruction of Lipopolysaccharide: Dry-Heat destruction kinetics" Applied and environmental Microbiology 36 (5): pp. 710-714, 1978.*
NPL "E-396" : Tsubokura A et al. entitled "*Paracoccus* . . . Gram-negative astaxanthin-producing bacterium" International J Systematic Bacteriology 49: pp. 277-282, 1999.*
Internaitonal Preliminary Report on Patentability for PCT Patent App. No. PCT/JP2006/326361 (Jul. 1, 2008).
First Office Action from Chinese Patent App. No. 200680049081.8 (Apr. 19, 2010) with English translation.
Office Action from Vietnamese Patent App. No. 1-2008-01601 (Aug. 12, 2010).
Supplemental European Search Report for EP Patent App No. 06843732.6 (Mar. 12, 2010).
Communication Pursuant to Article 94(3) EPC for EP Patent App. No. 06843732.6 (Apr. 1, 2010).
Office Action from Mexican Patent App. No. MX/a/2008/008524 (Aug. 23, 2011), with English translation.
Communication Pursuant to Article 94(3) EPC for EP Patent App. No. 06843732.6 (Dec. 8, 2011).

* cited by examiner

*Primary Examiner* — Humera Sheikh
*Assistant Examiner* — Bhaskar Mukhopadhyay
(74) *Attorney, Agent, or Firm* — Shelly Guest Cermak; Cermak Nakajima LLP

(57) ABSTRACT

An inexpensive heat treatment method for producing dried microbial cells is provided, wherein the method does not result in lowering the quality of the microbial cells or causing pulverization. The method includes a step of heating microbial cells to between 200 to 450° C. for 1 to 30 seconds.

7 Claims, No Drawings

METHOD FOR PRODUCING DRIED MICROBIAL CELLS

This application is a continuation under 35 U.S.C. §120 to PCT Patent Application No. PCT/JP2006/326361, filed on Dec. 27, 2006, which claims priority under 35 U.S.C. §119 to Japanese Patent Application No. 2005-378818, filed Dec. 28, 2005, both of which are incorporated by reference.

BACKGROUND OF THE INVENTION

1. Field of the Invention

The present invention relates to a method for producing dried microbial cells by subjecting a variety of fermentation microbial cells and microbial cells in activated sludge or the like to a heat treatment without lowering the quality thereof.

2. Brief Description of the Related Art

A method in which microbial cells in a fermentation broth are concentrated by membrane filtration or using a centrifuge or the like, and the resulting dense microbial cell suspension was dried by spraying in a fluidized dryer is generally used.

For example, in Patent document 1 (JP-A-5-123165), a method in which a suspension of an amino acid fermentation microorganism is dried using a rotary disc evaporator, followed by further drying using a closed dryer has been disclosed. In this method, dried microbial cells are prepared in a flake form for the purpose of improving the handling of the dried microbial cells which are conventionally in a fine powder form, and heating is performed at a high temperature for 1 hour or more using steam in both two drying steps.

SUMMARY OF THE INVENTION

As described above, in conventional drying of microbial cells, because heating is performed at a high temperature for a long time, the quality of dried microbial cells is lowered, for example, coloring of dried microbial cells accompanied by the Maillard reaction is liable to be caused and the color of the microbial cells changes to dark brown. In addition, an amino acid in the microbial cell protein, particularly lysine, which is most easily affected by heat although it is an essential amino acid, is degraded by heat during drying. Further, in spray drying, microbial cells are dried after they are pulverized, therefore, the resulting microbial cells are liable to be in the form of a dust, and the handling thereof is difficult, and moreover, the necessity of taking the risk of dust explosion into account arises. Further, because the productivity thereof is low, the cost required for drying is high.

Other than this method, there is a method in which an obtained dense microbial cell suspension, or a microbial cell cake obtained by further subjecting a dense microbial cell suspension to compression filtration by filter press or the like is dried using a drum dryer, however, the equipment productivity is low and the cost is high.

The present inventors conducted intensive studies in order to produce dried microbial cells through an inexpensive heat treatment method without lowering the quality of the microbial cells or causing a problem of pulverization by solving these problems.

As a result, while rapidly transferring a raw material using an extruder, the raw material was continuously fed on a screw which can perform mixing, kneading and heating, and a treatment was carried out under an instantaneous (1 to 30 seconds) heating condition such that the temperature of the raw material in the screw reached an ultra-high temperature (200 to 450° C.). To be more specific, an ultra-high temperature instantaneous heating was carried out by a method in which a raw material was rapidly transferred through a feed port in a screw while heating with a temperature gradient, and the raw material reached an outlet port of the screw was released into the atmosphere (1 atm) as such without applying a pressure.

Here, an important point in this heat treatment is that an open system is provided without attaching a die (an opening control valve) installed at a tip end of the extruder screw, and a pressure is not applied to the heated raw material at a tip end of the outlet port. Only by doing this can realize such instantaneous (1 to 30 seconds) heating at an ultra-high temperature (200 to 450° C.). In a general method using an extruder, a die (an opening control valve) is installed at an outlet port of a screw, and a heated raw material passes through a slit, whereby a pressure at a tip end or a retention time is controlled and a sterilization treatment is effected. However, a retention time is prolonged in a state in which a pressure is applied to a tip end, and when heating is carried out at an ultra-high temperature (200 to 450° C.), almost all the microbial cell protein is burned and it cannot function at all as a protein.

The present invention was made based on these findings, and is intended to provide a method for producing dried microbial cells characterized by feeding microbial cells into an extruder and subjecting the microbial cells to a heat treatment therein for 1 to 30 seconds such that the temperature of the microbial cells reaches 200 to 450° C.

In the method for continuous drying of an instantaneous (1 to 30 seconds) heat treatment at an ultra-high temperature (200 to 450° C.) using an extruder of the present invention, a retention time required for drying is extremely short, therefore, the quality of the dried microbial cells is hardly lowered, or rather improved.

For example, dried microbial cells hardly deteriorated due to browning, or the nutritional value thereof is not lowered. A decrease in an amino acid in the microbial cell protein, particularly lysine is not caused. In addition, the digestibility of the microbial cell protein is improved and the like. The microbial cells are discharged from the outlet port of the screw of the extruder after heating, and at the same time, the water contained therein is instantaneously vaporized while taking the heat of vaporization, and accompanying this, the microbial cells are dried while drastically lowering the temperature of the microbial cells. Due to this, even if the microbial cells are not intentionally cooled immediately after drying, a decrease in the quality is hardly caused.

Further, the dried microbial cells can be obtained in a granular form, therefore, the handling of the product is extremely favorable, and also there is no risk of dust explosion or the like.

Further, the retention time of heating is extremely short, therefore, the equipment productivity is high, and the cost required for drying can be reduced.

In this way, the heat treatment method according to the present invention can solve a lot of problems as in the above, therefore, it can be an extremely effective and advantageous drying method.

DESCRIPTION OF THE PREFERRED EMBODIMENTS

An apparatus to be used in the production method of the present invention is not particularly limited. An apparatus capable of performing a heat treatment at a predetermined temperature and giving a predetermined heated time can be used. As a preferred example of a practical apparatus, an extruder can be exemplified. Incidentally, as the extruder, any can be used as long as it can perform heating to 200 to 450° C., and a commercially available one can be used as such or after being modified.

In the present invention, microbial cells are heated to about 200 to 450° C. for about 1 to 30 seconds, and the temperature of 200 to 450° C. means the temperature of the microbial cells in a strict sense.

A preferred heating temperature is from about 250 to 400° C. (in terms of the temperature of the microbial cells), more preferably from 250 to 370° C., and particularly preferably from 280 to 350° C. Further, a preferred heating time is from about 1 to 20 seconds, more preferably from 5 seconds to 15 seconds, and particularly preferably from about 2 to 10 seconds. The heating temperature can be controlled by adjusting a heater installed in an extruder, and the heating time can be controlled by adjusting a feed rate of microbial cells and a rotation speed of a screw. However, it is difficult to allow microbial cells to pass through the extruder within 1 to 30 seconds. Accordingly, as the countermeasure, a die installed at the end of a discharge outlet of the extruder is uninstalled or the extruder is displaced with an extruder with a larger discharge outlet port diameter or the like, whereby the transfer rate in the extruder is accelerated. Further, heating to 200 to 450° C. is performed not for the entire inner side of the extruder, but for a part thereof. In the case where the heating site is determined to be an upstream or a midstream, it is necessary to cool a downstream side thereof to lower than 200° C., therefore, the heating site may be determined to be a downstream side (a side of the discharge outlet port).

Examples of the microbial cells to be a raw material in the present invention include fermentation microbial cells which are grown for performing fermentation of various amino acids such as glutamic acid, glutamine, lysine, arginine, phenylalanine and threonine (*Brevibacterium flavam, Brevibacterium lactofermentum, Corynebacterium glutamicum, Escherichia coli* and the like), fermentation microbial cells which are grown for performing fermentation of various nucleic acids such as inosine and guanosine (*Bacillus subtilis* and the like), microbial cells in activated sludge and the like. Other than these, common microbial cells such as bacteria, fungi and yeast can also be dried by heating, and microorganisms are not particularly limited.

These fermentation microbial cells grown in a fermentation broth is usually concentrated and dehydrated by subjecting the fermentation broth to membrane filtration or centrifugation, and optionally with the use of a compression filtration machine or the like, and by using the resulting concentrated and dehydrated matter as a raw material, drying by heating can be effected more efficiently. The content of water in the microbial cells before heating to be a raw material is generally from 20 to 90% (10 to 80% in terms of a solid content), preferably from 40 to 60% (40 to 60% in terms of a solid content).

The form of the dried microbial cells to be obtained by the heat treatment method of the present invention can be changed depending on the water content. That is, when the water content is less than about 5%, the form results in a powder, when the water content is from about 5 to 15%, the form results in a granule, and when the water content is about 15% or more, the form results in a clump.

EXAMPLES

Hereinafter, the present invention will be specifically described with reference to the following Examples. Incidentally, the in vitro evaluation items in Examples were carried out according to the following methods.

Example 1

Method for In Vitro Measurement

Measurement of amount of total nitrogen in microbial cells
About 5 g of a sample of microbial cells was pulverized in a mortar, and an about 20 mg portion was accurately weighed. The amount of total nitrogen in the weighed sample was determined using a high sensitive N,C-ANALYZER SUMI-GRAPH NC-800 autoanalyzer manufactured by Sumika Chemical Analysis Service, Ltd. The amount was determined by subjecting a sample to complete combustion (840° C.) in pure oxygen gas, and analyzing the nitrogen gas and carbon dioxide gas which are produced by gas chromatography. By multiplying the amount of total nitrogen N (%) by 6.25 (g/g), which is a protein conversion coefficient, the total protein content in the microbial cells (P0 (%)) was calculated using the following general formula (1):

$$P0(\%)=N(\%)\times 6.25 \qquad (1)$$

Measurement of Water-Soluble Protein (WSP)

The microbial cells were used above in the analysis of total nitrogen were placed in a 50 ml conical tube manufactured by FALCON CO., LTD., and subjected to a heat treatment. After the heat treatment, 4.00 g of the sample was weighed, about 40 ml of water was added to the sample, and the mixture was stirred. After the pH of the mixture was confirmed to be within 6.2 to 6.8 (when the pH was outside of this range, it was adjusted with a dilute hydrochloric acid or a dilute aqueous sodium hydroxide solution), water was added to bring the final volume to 50 ml, and then the conical tube was capped. This conical tube was placed on a receiprocal shaker at 40° C. and 100 rpm for 90 minutes, and immediately thereafter, was centrifuged at 3,000 rpm for 10 minutes to separate the supernatant from the pellet residue. The recovered supernatant was further filtered through a Millipore filter with a pore size of 0.45 μm (Cellulose Acetate Filter; manufactured by Toyo Roshi Kaisha, Ltd.), and the amount of water soluble protein ("WSP") was measured in the filtrate. In addition, the amount of solubilized protein (using a digestive enzyme (pepsin)) was measured in the residue. The protein (P1(%)) content was calculated using the general formula (1) from the amount of total nitrogen (N1(%)) in the heat-treated sample based on the measurement of the amount of total nitrogen in the microbial cells.

(2) Measurement

An aqueous solution of soluble soybean protein (protein content: 61.8%) was used as a standard. The Bradford colorimetric method using a kit manufactured by Bio-Rad Laboratories was used to measure the concentration (Cp (g/L)) of water-soluble protein in the filtrate obtained in the above-described method. Based on the concentration of the WSP, the amount of the WSP (g) in the filtrate was calculated using the general formula (2):

$$WSP(g)=Cp(g/L)\times 50/1000(L) \qquad (2)$$

Calculation Method for the Amount of Insoluble Protein (ISP)

The amount of insoluble protein (ISP) (g) was obtained by calculating the difference between the amount of protein (P1 (g)) in 4.00 g of the heat-treated sample and the amount of water-soluble protein (WSP (g)) dissolved in the aqueous solution, as follows:

$$ISP(g)=P1(g)-WSP(g)=4.00\ g\times N1(\%)/100\times 6.25(g/g)-WSP(g) \qquad (3)$$

Calculation Method for Index Item [A]
The index item [A] represents the ratio of ISP to WSP.

$$\text{Index item } [^A](g/g)=ISP(g)/WSP(g) \qquad (4)$$

Example 2

Measurement of Amount of Protein Solubilized by a Digestive Enzyme (PSP) of Insoluble Protein (ISP)

(1) About 20 ml of water was added to the residue (insoluble protein (ISP)) obtained by the above-described procedure and mixed, resulting in a slurry liquid. Then, 6 N hydrochloric acid was added to adjust the pH to 2.0, and then water was added to bring the volume to 40 ml.

A conical tube containing this mixture was capped and placed on a reciprocal shaker at 37° C. and 100 rpm for about 10 minutes until the temperature reached 37° C.

(2) When the temperature and pH settled at a constant value, 0.50 g of a digestive enzyme powder (pepsin:Pepsin 1:10,000 from porcine stomach mucosa manufactured by Wako Pure Chemicals), which had been weighed in advance, was added and mixed vigorously by a hand for a short time (about 15 seconds) to dissolve the digestive enzyme (hereinafter referred to as the slurry liquid for enzymatic degradation). Immediately thereafter, about 0.3 ml of the resulting liquid was sampled, and filtered through a Millipore filter with a pore size of 0.45 μm within 1 minute, so that the enzymatic degradation does not practically begin. Hence, a filtrate (1) free of ISP residue was obtained.

(3) The remaining slurry liquid for enzymatic degradation was shaken at 37° C. and 100 rpm, and insoluble protein (ISP) was solubilized by pepsin for 60 minutes. Immediately after completion of the reaction, an about 0.3 ml portion of the reaction solution was sampled, and filtered through a Millipore filter with a pore size of 0.45 μm in the same manner as in step (2). Hence, a filtrate (2) was obtained which can be used to measure the amount of solubilized protein.

(4) About 20 mg of each of the filtrate (1) and filtrate (2) obtained in steps (2) and (3) were accurately weighed, and amount of total nitrogen in each of the filtrates was analyzed using the highly sensitive NC-ANALYZER SUMIGRAPH NC-800 autoanalyzer manufactured by Sumika Chemical Analysis Service, Ltd. The respective analytical values Nb (%) and N60(%) were obtained.

(5) From the analytical values of total nitrogen before and after the reaction, Nb (%) and N60(%), the amount of protein solubilized after 60 minutes among the insoluble protein (ISP) (the amount of solubilized protein (PSP) (g) of ISP) was calculated using the following general formula (5):

$$PSP(g)=[N60(\%)/100-Nb(\%)/100]\times 6.25(g/g)\times 40\ ml\times density\ 1.00(g/ml) \quad (5)$$

(6) The ratio of PSP (g) to (ISP) (g) was calculated using the following formula to obtain an index item [B]:

$$Index\ item\ [B](g/g)=PSP(g)/ISP(g) \quad (6)$$

Example 3

*Escherichia coli* WC196 strain (which was deposited as *Escherichia coli* AJ13069 strain at the National Institute of Bioscience and Human-Technology, Agency of Industrial Science and Technology on Dec. 6, 1994 (at present, the Patent Organism Depository Center, the National Institute of Advanced Industrial Science and Technology, Central 6, 1-1-1 Higashi, Tsukuba, Ibaraki 305-8566, Japan)) and given an accession number of FERM P-14690. The deposit was converted to an international deposit under the Budapest Treaty on Sep. 29, 1995, and given an accession number of FERM BP-5252. This lysine-producing microorganism was cultured, and a fermentation broth was obtained. After the fermentation microorganisms in the fermentation broth were killed by heating (120° C., 3 min), the lysine-producing microorganisms were concentrated by common membrane filtration and centrifugation, producing a dense lysine-producing microbial cell suspension (solid content: 20%) with a water content of 80%. Furthermore, this suspension was dehydrated using a compression filtration machine, producing a microbial cell cake with a water content of 60%. Incidentally, the dense microbial cell suspension with a water content of 80% was dried using a fluidized dryer (a turbo dryer manufactured by VOMM) (drying conditions:blast temperature of 185° C., temperature of microbial cells of 107° C., and retention time of 25 minutes), producing dried microbial cells with a water content of 5.2% (Test section 1). The dense microbial cell suspension with a water content of 80% and the microbial cell cake with a water content of 60% were both separately subjected to heating, and then drying using an extruder. Incidentally, the extruder used was a twin screw laboratory extruder: "Mark II" (screw size: length of 450 mm, and opening diameter of 30 mm) manufactured by The Japan Steel Works, Ltd., in which a die at an outlet port of the screw had been uninstalled. A screw rotation speed of 400 rpm was used. For the dense microbial cell suspension with a water content of 80%, dried microbial cells were obtained, however, the productivity was extremely low (see Test section 2). The heating and drying of microbial cell cake with a water content of 60% obtained by further performing compression filtration of the dense microbial cell suspension with a water content of 80% was carried out under the following conditions: the temperature of the microbial cells was set to 300° C. and the heating time was set to 15 seconds (Test section 3), 10 seconds (Test section 4), and 5 seconds (test section 5); the temperature of the microbial cells was set to 400° C. and the heating time was set to 7 seconds (Test section 6); the temperature of the microbial cells was set to 250° C. and the heating time was set to 20 seconds (Test section 7); and the temperature of the microbial cells was set to 200° C. and the heating time was set to 25 seconds (Test section 8). As a result, the drying was extremely efficient. The quality of the respective dried lysine fermentation microbial cells obtained in each of the Test sections was evaluated, and is shown in Table 1.

TABLE 1

Quality of dried microbial cells

| Test section | Water content in microbial cells (%) | Heating and drying method | Heating and drying conditions Temperature of the microbial cells (° C.) | Time | Water content (%) | Coloring degree | Form | Particle size (mm) | Recovery rate of lysine in protein (%) |
|---|---|---|---|---|---|---|---|---|---|
| 1 | 80 | Fluidized drying | 107 | 25 min | 5.2 | 5 | Fine powder | 0.2 pass | 76 |
| 3 | 60 | Present invention | 300 | 15 sec | 6.8 | 3 | Powder | 0.2 to 0.5 | 94 |
| 4 | 60 | Present invention | 300 | 10 sec | 8.1 | 2 | Granule | 1 to 3 | 98 |
| 5 | 60 | Present invention | 300 | 5 sec | 30 | 2 | Clump | 5 to 8 | 99 |
| 6 | 60 | Present invention | 400 | 7 sec | 9.0 | 2 | Granule | 1 to 3 | 96 |

TABLE 1-continued

Quality of dried microbial cells

| Test section | Water content in microbial cells (%) | Heating and drying method | Heating and drying conditions | | Water content (%) | Coloring degree | Form | Particle size (mm) | Recovery rate of lysine in protein (%) |
|---|---|---|---|---|---|---|---|---|---|
| | | | Temperature of the microbial cells (° C.) | Time | | | | | |
| 7 | 65 | Present invention | 250 | 20 sec | 8.4 | 2 | Granule | 1 to 3 | 98 |
| 8 | 65 | Present invention | 200 | 25 sec | 8.8 | 2 | Granule | 1 to 3 | 98 |
| Raw material | 60 | Microbial cell cake before drying | | | 60 | 1 | Sheet | | 100 |

The following ranking of coloring was used after heating and drying:

1: before drying; 2: somewhat colored; 3: colored; 4: strongly colored; 5: burned state Analysis of recovery rate of lysine in dried microbial cell protein:

5.0 g of lysine microbial cells were subjected to a heat treatment at 103° C. for 24 hours in 6 N hydrochloric acid, and then the released lysine was determined by performing an analysis using an amino acid analyzer.

As shown in the table, it is found that the dried microbial cells obtained by the heating and drying method according to the present invention are hardly colored and show little decrease in lysine in the microbial cell protein. Further, the obtained dried microbial cells are in a granular form, and the working environment is not deteriorated due to fine powder, therefore, on-site handling thereof is easy. Further, the retention time in heating is as short as about 15 seconds, which is one-hundredth that of the fluidized drying method. Therefore, because the productivity of heating and drying is extremely high, a product can be obtained at a low cost.

With regard to the dried microbial cells obtained in the above test sections, 1, 3, 4 and 5, dried microbial cells obtained as a result of performing heating of the microbial cell cake with a water content of 60% obtained by further performing compression filtration of the dense microbial cell suspension with a water content of 80% under the following conditions: the temperature of the microbial cells was set to 200° C. and the heating time was set to 15 seconds (Test section 9), the temperature of the microbial cells was set to 200° C. and the heating time was set to 5 seconds (Test section 10), the temperature of the microbial cells was set to 250° C. and the heating time was set to 15 seconds (Test section 11), the temperature of the microbial cells was set to 250° C. and the heating time was set to 5 seconds (Test section 12), the temperature of the microbial cells was set to 350° C. and the heating time was set to 15 seconds (Test section 13), the temperature of the microbial cells was set to 350° C. and the heating time was set to 5 seconds (Test section 14), the temperature of the microbial cells was set to 400° C. and the heating time was set to 15 seconds (Test section 15), and the temperature of the microbial cells was set to 400° C. and the heating time was set to 5 seconds (Test section 16), and the lysine fermentation microbial cell cake before heating and drying, a bypass property in ruminants (corresponding to a parameter [A]), a digestibility (corresponding to a parameter [B]), and the effectiveness of protein in the small intestine of ruminants (corresponding to a parameter [A]·[B]) were evaluated by an in vitro test, and the results are shown in Table 2.

TABLE 2

| Test section | Heating and drying method | Heating and drying conditions | | Water content (%) | Content (%) of total protein (P) | Content (WSP/P) of Water-soluble protein (WSP) | In vitro evaluation | | | Remarks |
|---|---|---|---|---|---|---|---|---|---|---|
| | | Temperature of the microbial cells (° C.) | Time | | | | [A] g/g | [B] g/g | [A] · [B] | |
| 1 | Fluidized drying | 107 | 25 min | 5.2 | 73.1 | 2.8 | 34.7 | 0.33 | 11.5 | Control example |
| 3 | Present invention | 300 | 15 sec | 6.8 | 76.1 | 2.6 | 37.5 | 0.49 | 18.4 | Example |
| 4 | Present invention | 300 | 10 sec | 8.1 | 75.3 | 2.8 | 34.7 | 0.48 | 16.7 | Example |
| 5 | Present invention | 300 | 5 sec | 30 | 59.1 | 3.1 | 31.3 | 0.43 | 13.5 | Example |
| 9 | Present invention | 200 | 15 sec | 20.5 | 67.0 | 2.4 | 40.7 | 0.31 | 12.6 | Example |
| 10 | Present invention | 200 | 5 sec | 45.0 | 46.9 | 3.5 | 27.6 | 0.37 | 10.2 | Example |
| 11 | Present invention | 250 | 15 sec | 15.7 | 71.7 | 2.6 | 37.5 | 0.43 | 16.1 | Example |
| 12 | Present invention | 250 | 5 sec | 37.0 | 54.5 | 3.2 | 30.3 | 0.41 | 12.4 | Example |
| 13 | Present invention | 350 | 15 sec | 3.1 | 79.2 | 2.2 | 44.5 | 0.39 | 17.4 | Example |

TABLE 2-continued

| Test section | Heating and drying method | Temperature of the microbial cells (°C.) | Time | Water content (%) | Content (%) of total protein (P) | Content (WSP/P) of Water-soluble protein (WSP) | In vitro evaluation [A] g/g | [B] g/g | [A]·[B] | Remarks |
|---|---|---|---|---|---|---|---|---|---|---|
| 14 | Present invention | 350 | 5 sec | 5.0 | 79.1 | 2.9 | 33.5 | 0.66 | 22.1 | Example |
| 15 | Present invention | 400 | 15 sec | 2.1 | 79.1 | 1.7 | 57.8 | 0.17 | 9.8 | Example |
| 16 | Present invention | 400 | 5 sec | 1.2 | 80.1 | 2.2 | 44.5 | 0.28 | 12.5 | Example |
| Raw material | Microbial cell cake before drying | | | 60 | 32.2 | 10.3 | 8.7 | 0.37 | 3.2 | Control example |

As is apparent from the above results, the [B] value which is a parameter showing the digestibility of dried microbial cell protein obtained by the heat treatment method according to the present invention was improved in almost all the test sections compared with the case of dried microbial cell protein obtained by a conventional drying method. Accordingly, drying of the microbial cells as well as the quality of the microbial cell protein were improved, and it was confirmed that the dried microbial cell protein obtained by the heat treatment method according to the present invention was effective as an additive for feed. Further, the [A]·[B] value which is a parameter showing the effectiveness of protein in the small intestine of ruminants was also improved in almost all the test sections, and thus, it was confirmed that they were effective also as a feed for ruminants.

Industrial Applicability

The dried microbial cells obtained in the present invention are low in deterioration of protein and can be used as an additive for feed and the like.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

The invention claimed is:

1. A method for producing dried microbial cells comprising heating microbial cells to between 250 to 400 degree C. for 1 to 30 seconds in an extruder while avoiding burning, wherein the dried microbial cells are *Escherichia coli*.

2. The method for producing dried microbial cells according to claim 1, wherein said heating is carried out for 1 to 20 seconds, and the temperature of the microbial cells is between 250 to 370° C.

3. The method for producing dried microbial cells according to claim 1, characterized in that the water content of the dried microbial cells after said heating is from 5 to 15%.

4. An animal feed comprising the dried microbial cells produced by the method of claim 1.

5. Dried microbial cells produced by the method of claim 1.

6. Dried microbial cells produced by the method of claim 2.

7. Dried microbial cells produced by the method of claim 3.

* * * * *